United States Patent
Sadik et al.

(10) Patent No.: US 6,602,989 B1
(45) Date of Patent: Aug. 5, 2003

(54) SYNTHESIS, CHARACTERIZATION, AND APPLICATION OF PYRIDYLAZO BIOCONJUGATES AS DIAGNOSTIC AND THERAPEUTIC AGENTS

(75) Inventors: Omowunmi A. Sadik, Vestal, NY (US); Hongwu Xu, Binghamton, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 09/573,993

(22) Filed: May 17, 2000

(51) Int. Cl.⁷ ............ C07K 17/10; C07K 17/12; A61K 51/00; G01N 33/20; G01N 33/548; C12N 9/96

(52) U.S. Cl. ............ 530/403; 424/1.53; 435/7.94; 435/188; 436/74; 436/529; 436/530; 436/804; 530/391.1; 530/391.5

(58) Field of Search ............ 435/188, 7.94; 530/391.5, 403, 391.1; 436/530, 529, 804, 74; 424/1.53

(56) References Cited

U.S. PATENT DOCUMENTS 4,448,763 A 5/1984 Triplett
5,459,040 A 10/1995 Hammock et al.
5,925,570 A 7/1999 Nishidate et al.

OTHER PUBLICATIONS

N. Babaev et al, Chemical Abstract No. 87: 94917 (1977).*

Sh. Talipov et al, Chemical Abstract No. 67: 29028 (1967).*

* cited by examiner

*Primary Examiner*—Mary E. Ceperley
(74) *Attorney, Agent, or Firm*—Salzman & Levy

(57) ABSTRACT

The detection of gallium in biological samples is required due to its role in the diagnosis of tumor and for possible treatment of malignancies. However, the use of purely instrumental techniques is unsuitable for detection of low levels of gallium in biological matrices. New protein conjugates have been synthesized based on 4-(2-pyridylazo) ligands. The conjugates detect gallium in biological matrices using a non antibody-based sandwich assay format. The recovery level is between 97–101.3 with a relative standard deviation of less than 5%. The assay results in a detection limit of $5 \times 10^{-8}$ M and a remarkable selectivity for gallium (III) relative to other metals investigated. The new method provides adequate accuracy for gallium applicable for animal physiology and clinical toxicology.

7 Claims, 9 Drawing Sheets

1.

2.

3.

4.

5.

6.

7.

8.

9.

1. Albumin

2. Albumin

3. Horseradish peroxidase

4. Alkaline phosphatase

4 Parameters  $y = (a-d)/(1+(x/c)^b)+d$
$a=0.02419\ b=3.951\ c=3.389\ d=0.3646$
$R=0.9980\ R^2=0.9961\ err=0.006578$

SYNTHESIS, CHARACTERIZATION, AND APPLICATION OF PYRIDYLAZO BIOCONJUGATES AS DIAGNOSTIC AND THERAPEUTIC AGENTS

This invention was made with Government support under Grant R825323-01-0 awarded by the United States Environmental Protection Agency. The Goverment has certain rights in the invention.

FIELD OF THE INVENTION

This invention relates to the production of binary and ternary protein-metal complexes and their utility as diagnostic and therapeutic agents and, more specifically, to the formation of protein conjugate-gallium(III) binary complexes and protein conjugate-gallium(III)-enzyme conjugate ternary complexes to provide in vitro or in vivo quantitative determination of gallium ion in body fluids and a means to transport therapeutic dosages of radioisotopes of gallium to localized, diseased body sites.

DEFINITIONS AND ABBREVIATIONS

To facilitate the understanding of this specification and the appended claims, definitions to various words and phrases are provided.

Binary Complex is a metal ion chelated with one ligand.

Chelators are part of a proteinaceous conjugate and are able to donate electrons and combine by coordinate bonding with a metal ion to form complexes.

Conjugate is an organic polymer, specifically a proteinaceous material having an exogenous ligand or chelating functionality covalently bound to the polymer.

Exogenous chelating group is a chelating group that is not present in the native protein molecule.

Ligand is an organic compound that has one or more sites to covalently bond to a metal ion (i.e., bidentate: two sites per ligand; tridentate: three sites per ligand).

Radioisotopes are radionuclide metal ions having a known half-life.

Ternary Complex is a complex composed of a metal ion chelated with two ligands, which may be identified or different.

BACKGROUND OF THE INVENTION

The use of radiopharmaceutical Ga-containing compositions to image and diagnose tumor formations by tumor tomography and to treat malignancies has been well documented. For example, Gallium-67, as the carrier-free citrate, is used routinely in clinical medicine in diagnosing, staging, and monitoring several neoplastic disease states. Antitumoral therapeutic effects of gallium(III) nitrate have also been widely demonstrated in laboratory animals; and the low degree of toxicity would appear to suggest its suitability for treating various tumors. Several workers have shown that when the concentration of Ga is increased, tumor mass is decreased.

Unfortunately, this agent is plagued with imaging problems which are related to plasma protein binding. Specifically, gallium has an affinity for blood and soft tissue proteins. When given in very low doses, it is extensively bound to non-target sites (see U.S. Pat. No. 4,448,763).

Furthermore, the mechanism of gallium uptake during tumor detection is still largely unknown. It appears that the nature and types of anionic species present are the determining factors responsible for the distribution of gallium in the various organs.

In addition, most of the available instrumental methods for determining gallium are expensive and unsuitable for gallium detection in biological samples. They exhibit poor selectivity due to interference from other metals. These include inductively-coupled plasma spectroscopy (ICP), atomic absorption spectroscopy (AAS), and neuron activation coupled with high-resolution spectrometry. A comparative investigation of the suitability of AAS, emission spectroscopy with arc and hollow cathode excitation sources for detecting gallium in biological samples indicated that all three methods are significantly influenced by matrix effects. Hollow cathode emission was found to be influenced, to a lesser extent, by matrix effects but was more precise than the other two detection methods.

In view of the widespread medical application, analytical methods are required which are capable of accurately determining gallium concentrations in different biological samples (e.g., at target sites and in the blood and soft tissue).

Gallium has been incorporated into binary protein conjugates. However, prior art processes often must overcome incompatibility between the uncomplexed gallium salt and the protein conjugate. At appropriate pH values that do not cause denaturization of the protein, gallium salts tend to precipitate as gallium hydroxide. Therefore, special procedures must be employed to keep the formulations homogeneous (see U.S. patent application, Ser. No. 650,127).

Several metals, including mercury, indium, and cadmium, can be detected by using antibodies formed against ethylenediamine tetra acetic acids (EDTA). These antibodies (Abs) are usually produced from haptens obtained from the derivatization of EDTA with large proteins such as bovine serum albumin (BSA), keyhole limpet hemocyanin (KLH) or synthetic peptides. However, such derivatization often significantly alters the properties of the antigen. The resultant Abs, particularly monoclonal antibodies, are likely to possess heterogeneous molecular composition comprising a number of "isoforms" which may be different in molecular structure, biological potency and physiological functions. In addition, the assay technologies largely depend on the availability of Abs, which are expensive to produce and limited by different antibody specificity and cross-reactivity patterns.

Therefore, non-antibody based detection methods provide an attractive alternative to immunochemical assays. U.S. Pat. No. 5,459,040 to Hammock, et al. describes a rapid and selective method for detecting and quantifying mercury. This process relies on the specific reaction of sulfur- and mercury-containing conjugates. The method in the Hammock et. al. patent requires no antibody; quantification depends on the amount of organometallic compound that is bound to a sulfur-mercury complex, and is inversely proportional to the quantity of metal ion present in the sample. The optical density response is also inversely proportional to the quantity of the metal ion present.

A recently issued patent, U.S. Pat. No. 5,925,570 to Nishidate, et al., describes a process for measuring the quantity of metals in samples of living bodies. That patent, which in many respects can be considered state-of-the-art, describes a process whereby quantification of an objective metal is determined after other metals are administered to release the objective metal. The quantification process involves the use of spectro optical measurements using color-generating indicator reagents that are metal specific.

Although that process can be used for diagnostic testing of metals in body fluids, it can not be used for therapeutic treatments requiring the transport of metal ions to a diseased site in the body.

The current state-of-the-art techniques for quantifying metals in vivo or in vitro, as hereinabove revealed, suffer from several deficiencies, namely: high cost, poor specificity if other metals are present (i.e., matrix interactions), and loss of metal due to non-target affinity.

SUMMARY OF THE INVENTION

Having described the current state-of-the-art and associated problems that still remain, it is an important aspect of the present invention to provide processes and materials that are used to deliver therapeutic medicines and to quantify concentrations of these medicines at the target and remote sites, in particular, the detection and quantification of gallium(III) ions in body fluids to assist in determining optimal dosage for gallium(III) radiotherapy of lesions and other illnesses.

Another aspect of the invention is to provide an analytical test for quantifying the level of gallium(III) with minimal interference from other metal ions that might be present, thereby eliminating the need for prior processing for removal of ancillary metal ions.

Another aspect of the invention is to provide a simple, rapid, and inexpensive process to quantify the level of gallium(III) in body fluids such as blood (whole blood, blood serum, blood plasma, blood cell), urine, feces, saliva, breast milk, and so on. Generally speaking, in clinical examination, metals contained mainly in blood or urine are measured in vivo and in vitro.

Another aspect of this invention is to provide a therapeutic ternary coordination complex from a protein conjugate-gallium(III) ion-enzyme conjugate where the protein has an affinity for an antigen from a cancerous lesion and wherein a therapeutic dose of radioactive gallium is localized at the lesion or tumor site. The preferred protein in this case is an antibody or antibody segment that has an affinity for the antigen.

Another aspect of the invention is to provide an enzyme conjugate that is specific to binding with a gallium(III) complex of a protein conjugate in order to form a ternary complex that is easily detected and quantifiable.

Another aspect is to use derivatives of pyridylazo resorcinol (PAR) and their protein conjugates to form tridentate complexing ligands with gallium(III) ions to quantify gallium metal in body fluids.

Another aspect of this invention provides methods for the preparing conjugates of proteins or polypeptides with metal ions. The resulting conjugates are useful as radiopharmaceuticals.

Another aspect of this invention is to provide binary and ternary protein conjugate-metal complexes possessing therapeutic and diagnostic value that can be administered to a patient, transported in the body, and adsorbed at diseased sites.

Another aspect of the invention is to provide a process to form protein-conjugates using derivatives of PAR.

To achieve the above described general aspects of the invention, the following specific objectives are enumerated: (i) to prepare metal-protein conjugates using 4-(2-pyridylazo)resorcinol (PAR), and (ii) to provide an analytical basis for discrimination of the resulting conjugates for detecting gallium. PAR has been used extensively to analyze metals. It possesses a variety of useful spectroscopic and luminescence properties. To our knowledge, the use of 2-pyridylazoresorcinol and its derivatives, such as 1-(2-pyridylazo)-2-naphthol (PAN), have not been employed to prepare biological conjugates. Compared to PAN, PAR was chosen as a modifier in our work because of its relative stability and higher solubility in water.

We hereby report novel binary and tertiary complexes useful for therapeutic and diagnostic treatments using protein-modified 2-pyridylazoresorcinol ligand derivatives (PAR) as the biorecognition element. PAR was derivatized with proteins and enzymes such as ovalbumin, bovine serum albumin (BSA), and alkaline phosphatase (AP) to generate the respective conjugates. In one embodiment the synthesis was carried out using a water-soluble carbodiimide and N-hydroxy succinamide coupling techniques. The results of characterization experiments using electrospray mass spectrometry, UV/vis spectroscopy, and Fourier transform infrared (FTIR) experiments confirmed that a new class of protein conjugates has been synthesized. The conjugates were used for detecting gallium in a sandwich enzyme-linked immunosorbent assay (ELISA) format. The detection format does not require the use of antibody, contrary to conventional immunoassay techniques. This method results in a remarkable selectivity for gallium(III) relative to other metals investigated, including Fe(II), Zn(II), In(III), Hg(II), Tl(III) and Pb(II).

BRIEF DESCRIPTION OF THE DRAWINGS

A complete understanding of the present invention may be obtained by reference to the accompanying drawings, when considered in conjunction with the subsequent detailed description, in which.

DESCRIPTION OF PREFERRED EMBODIMENTS

Metal Ions of Interest

Figure 1:
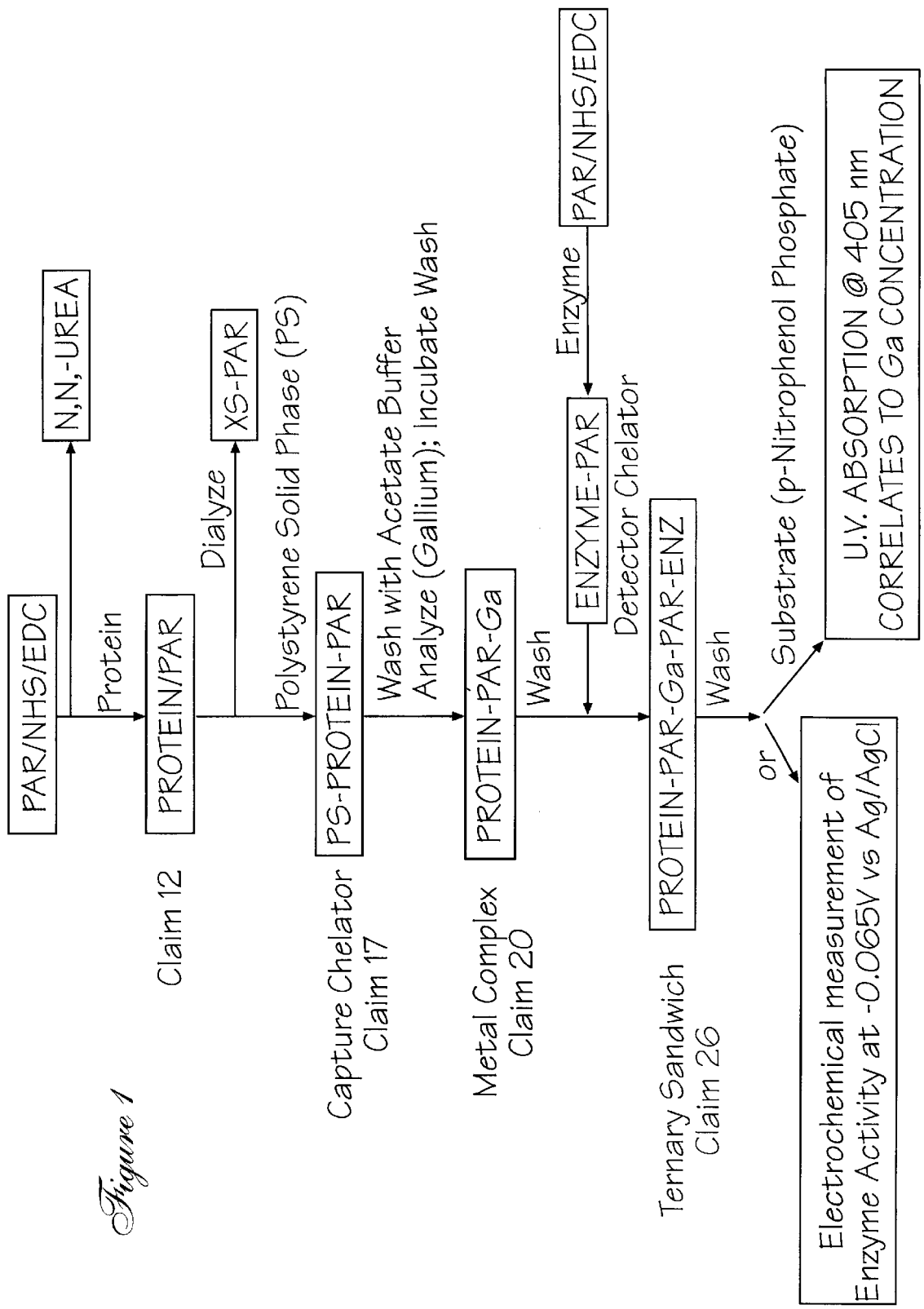
FIG. 1 depicts one embodiment of a series of process steps in manufacturing the protein conjugate-gallium(III) ion-enzyme conjugate ternary complex of the present invention.

Of particular interest to the present invention are metal ions that may be found in the human bloodstream. Such metals include endogenous, essential metal ions and non-physiologic metal ions that may be present either as a result of their use as therapeutics or because of the ingestion, absorption or inhalation of metals present in the environment. Thus, virtually all metal ions from magnesium (atomic number 12) to plutonium (atomic number 94); but in particular, lead, mercury, nickel, cadmium, thallium, antimony, silver, chromium, manganese, platinum, gold, aluminum, bismuth, gallium, iron, copper, zinc, cobalt, molybdenum, selenium, and vanadium ions, are amenable for use in this process.

Diagnostic radionuclides useful in the present invention include ruthenium-95, ruthenium-97, ruthenium-103, ruthenium-105, technetium-99m, mercury-197, gallium-67, gallium-68, osmium-191, indium-111, indium 113m and lead-203. Therapeutic radionuclides include palladium-103, palladium-109, silver-111, antimony-119, actinium-225, gold-198, gold-199, copper-67, rhenium-186, rhenium-188, rhenium-189, lead-212 and bismuth-212.

Among the radionuclides and labels useful in the methods of the present invention, gamma-emitters, positron-emitters, x-ray emitters and fluorescence-emitters are suitable for localization and/or therapy, while beta- and alpha-emitters and electron- and neutron-capturing agents, such as boron and uranium, also can be used for therapy.

For diagnostic or therapeutic purposes, the metal ion should be such that minimal radiation damage is caused to healthy tissue. In order to achieve this, radioactive metal ions are selected that decompose within a short period of time for example, several hours to 4 days, and do not decay to such an extent as to generate sufficient particles that cause significant collateral damage to surrounding healthy cells. A preferred metal ion in the current invention is gallium(III) and in particular radio isotopes such as $^{66}$Ga(III), $^{67}$Ga(III), $^{71}$Ga(III), $^{72}$Ga(III), or $^{73}$Ga(III)

These characteristics, coupled with the known therapeutic properties of gallium, and the contraindication that gallium (III) has an affinity for non-target sites, is the motivation to find alternative modes of delivery for gallium that will increase its selectivity for the target area and methods of quantifying gallium(III) in non-target areas in order to determine the safest regime for administering radiotherapy using gallium(III).

According to one preferred embodiment of the present invention, proteinaceous binary and ternary complexes of gallium are provided in order to improve target selectivity and also to provide accurate quantification of gallium(III) concentrations.

Ligands

The ligand-containing molecules of the present invention consist of a central metal ion bound to a number of other molecules, termed ligands. The nature of the chemical bond formed between a ligand and a metal can be thought of as involving the donation of a pair of electrons present on the ligand molecule or, in molecular orbital terms, as a molecular orbital formed by combining a filled orbital of the ligand with a vacant orbital of the metal. Those atoms in the ligand molecule that are directly involved in forming a chemical bond to the metal ion are therefore termed the donor atoms, generally comprising elements of Groups V and VI of the periodic table, with nitrogen, oxygen, sulfur, phosphorus and arsenic being those most commonly employed.

Molecules that contain two or more donor atoms capable of binding to a single metal ion are termed chelating agents, or chelators, and the corresponding metal complexes are called chelates. The number of donor atoms present in a given chelator is termed the denticity of that chelator, ligands possessing two donor sites being called bidentate, those with three donor sites, tridentate, and so forth. In general, the higher the denticity of a chelator the more stable are the chelates formed, up to the point at which the denticity of the chelator matches the maximum coordination number attainable by the particular metal ion of interest. The maximum coordination number of a given metal ion in a given oxidation state is an intrinsic property of that metal, reflecting the number of vacant orbitals and, hence, the number of chemical bonds it is able to form with ligand donor atoms. When all of the available vacant orbitals have been used to form bonds to donor atoms in the ligand or ligands, the metal is said to be coordinatively saturated.

For any given metal ion, useful ligands according to the present invention may be selected by one skilled in the art, employing the following criteria. Ligands must possess donor atoms (or sets of donor atoms in the case of chelating ligands) that favor binding to the target metal ion. The general preference of any given metal ion for particular donor atoms (generally selected from the group consisting of carboxylic, phenolic, or ether oxygen atoms, amine, imine, or aromatic nitrogen atoms and charged or neutral sulfur atoms) is well known in the art.

It is not essential that any of the exogenous ligands bound to an antibody, be chelating ligands, according to the present invention. Though ligands suitable for use in the present invention are preferably chelating ligands, the presence of a chelating ligand is not essential, as non-chelating ligands, such as certain phosphines and sugar analogs, can also be useful. These ligands can be either monodentate or of higher density.

The ligands must also offer the prospect of forming ligand-metal linkages that are likely to remain stable in vivo. That is, the ligand-metal linkage does not dissociate during the time required to raise an immune response to or perform quantification of the complex. For many metals of interest there exists considerable art relating to the in vivo stability of particular ligand-metal linkages, which may be used to guide ligand selection. This requirement favors the selection of chelating ligands, as chelating ligands generally form coordination complexes of higher thermodynamic stability than do corresponding combinations of monodentate ligands.

Within the scope of the present invention, there are many useful ligands that have been shown to coordinately bond to metal ions; they may either be mono, bi, or tridentate, depending on the number of sites that the ligand binds to the metal ion. Most preferred are ligands that are tridentate and contain a plurality of ligand sites. Useful chelating ligands that form highly stable complexes with many metal ions include pyridylazo resorcinol derivatives, polyaminopolycarboxylic acids such as ethylenediaminetetraacetic acid (EDTA) and diethylenetriaminepentaacetic acid (DTPA) and phenol-containing aminopolycarboxylates such as N,N'-bis (hydroxybenzyl)ethylenediamine-N,N'-diacetic acid (HBED), aminobenzyl derivatives of ethylenediaminetetraacetic acid derivatives (see U.S. Pat. No. 4,722,892 to Meares et al.), dihydroxydisulfonic acid derivatives (TIRON) (see U.S. Pat. No. 4,732,974 to Nicolotti, et al.). These chelators have a denticity of 3 or higher and, as most transition and main group metals have a maximum coordination number of 6, the resulting species are coordinatively saturated binary or ternary complexes (i.e., complexes consisting of a single to two ligand molecules and a single metal ion).

A further requirement is that each of the above described ligands be bifunctional. A bifunctional ligand is a molecule that contains, in addition to at least one metal binding site (donor atom), a second reactive moiety through which the ligand may be covalently linked to, for example, a protein, a solid phase or a label, without significantly affecting the metal-binding properties of the ligand. Reactive moieties include such groups as hydroxy, phenoxy, carboxy, and isothiocyanato.

One skilled in the art will readily recognize positions within a given ligand molecule where incorporation of an additional reactive moiety will not affect metal-binding properties. Such a skilled practitioner will also readily recognize reactive moieties that are useful in coupling the ligand to another molecule or solid phase. Typically, the sites for ligand complexation and covalent bonding are structurally and electronically isolated from each other so that there is no interference with their respective properties. The product of such reactions is designed to create at least one "exogenous chelating group" per polypeptide/protein chain.

Ligands should also be selected so that they contain a highly differentiated organic framework, incorporating wherever possible aromatic structures, rigid ring systems and asymmetric carbon centers. Having selected the donor atom set, denticity, bifunctional side arm and organic framework of the ligands, the stoichiometry of the resulting target metal ligand-containing complex, whether ternary or of higher molecularity is dictated by the maximum coordination number of the particular metal ion of interest.

Bifunctionality of the ligands is essential for configuring screening assays used to identify and select monoclonal antibodies that are specific for metal containing ligand complexes, for preparing affinity chromatography media used to purify such antibodies, and for preparing antigen-label tracers for use in immunoassays.

In addition to displaying bifunctionality and stable ligand-metal binding in vivo, preferred ligands also incorporate structural features that are thought to contribute to immunogenicity and differential recognition by proteins. Such structural features include aromatic ring systems (Zoller, et al, *J. Nucl. Med.*, 33, 1366–72 (1992)), rigid cyclic structures (Kosmas, et al, *Cancer Res.*, 52, 904–11 (1992)) and asymmetric carbon centers (Reardon, et al, *Nature*, 316, 265–68 (1985); Zoller, et al, *J. Nucl. Med.*, 33, 1366–72 (1992)).

The present invention preferably employs exogenous chelators based on derivatives of aza mono- and fused heterocyclic compounds having an azo linking group adjacent to the nitrogen atom in the heterocycle. A most preferred example is the use of pyridylazoresorcinol (PAR) and its derivatives as exogenous chelators. Examples of PAR derivatives that are illustrative, but not limiting, within the present invention are:

3-amino-4-[3-(1-methyl-2-piperidyl)-2-pyridylazo]phenol;
1-(2-pyridylazo)-2,7-naphthalenediol;
6,7-dihydroxy-5-(2-pyridylazo)-2-naphthalenedisulfonic acid;
2,6-diamino-3-(pyridylazo)pyridine;
4-(2-pyridylazo)methyl salicylic acid;
3-hydroxy-4-(2-quinolinylazo)phenol;
3-hydroxy-4-(2-pyrimidylazo)phenol; and
3-hydroxy-4-(2-benzimidazolylazo)phenol.

Figure 2:
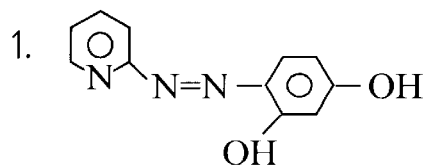
FIG. 2 depicts illustrative examples of ((heterocyclyl)azo) orthohydroxyarylene (PAR) derivatives.
Figure 2:
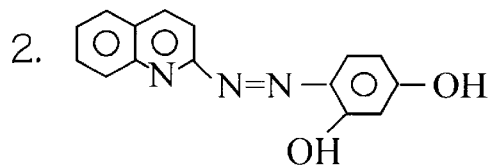
Figure 2:
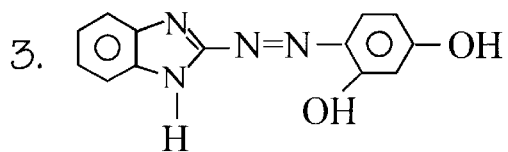
Figure 2:
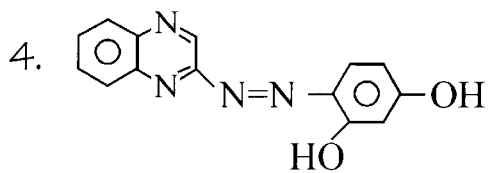
Figure 2:
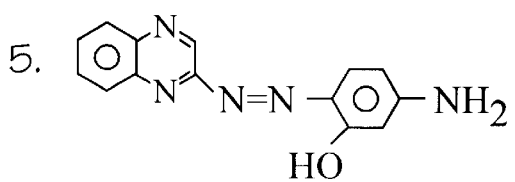
Figure 2:
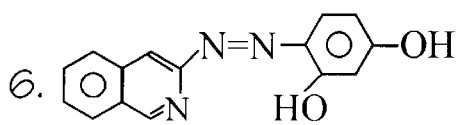
Figure 2:
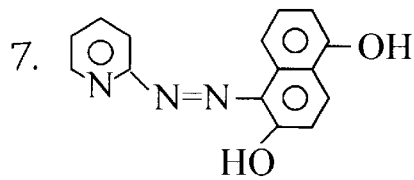
Figure 2:
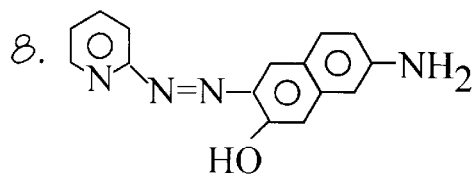
Figure 2:
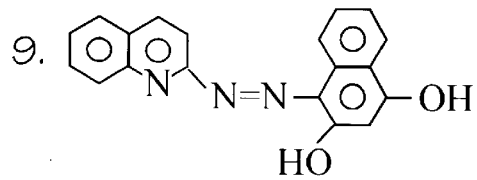
Figure 3:
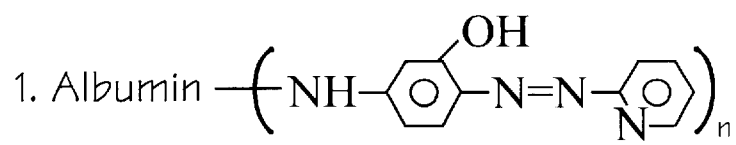
FIG. 3 depicts illustrative examples of Proteinaceous conjugates ($PC_1$)
Figure 3:
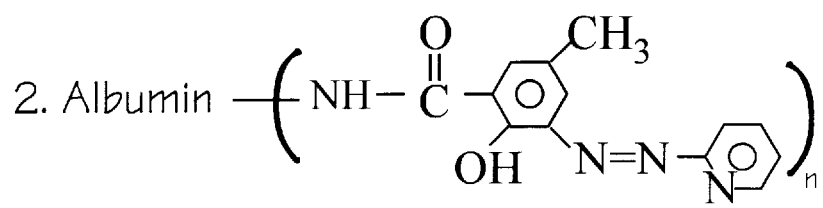
Figure 3:
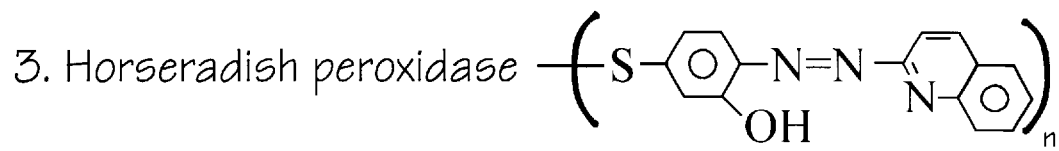
Figure 3:
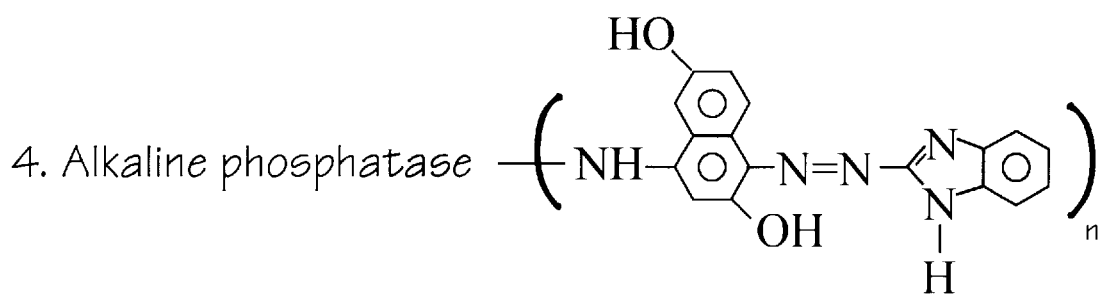

Other Examples of These ((heterocyclyl)azo)orthohydroxyarylene (PAR) derivatives are represented in FIG. 2. Within the scope of this invention are heterocyclic rings that have at least one heteroatom, itself having a lone pair of electrons, in a position adjacent to the site of the attachment of the aza functionality to the heterocycle. Likewise, the orthohydroxyarylene functionality can be generalized to require a heteroatom such as oxygen, nitrogen or sulfur attached to the ortho position (relative to the site of the aza functionality attachment) of the aryl ring. The hetero atom on the aryl ring will contain a lone pair of electrons and will comprise such moieties as hydroxyl, amino or sulfhydryl respectively.

These PAR derivatives are preferred compared to prior art chelators since they form relatively stable complexes and have acceptable solubility in water. As discussed hereinbelow in greater detail, these derivatives, when bound to proteinaceous materials, are highly selective to the metal ions to which they coordinately bind. Unexpectedly, the exogenous ligand-containing chelating functionalities of the protein conjugates bind essentially exclusively to gallium metal ions. This unique property allows these materials to detect gallium very accurately, even in the presence of other metal ions.

The stability of these metal complexed conjugated proteinaceous materials also allows them to be used in vivo and in vitro as diagnostic and therapeutic reagents. Prior art conjugates do not have the specificity for complexation to a given metal. Therefore, they suffer from the possibility of equilibration with other metal ions found in vivo, thereby causing either a deterioration in imaging quality or loss of therapeutic activity. In the case of in vivo diagnostic or therapeutic use, it is highly desirable to have the proteinaceous material be specific to a given antigen, thereby causing the metal complexed to be localized at the site where infection or disease predominates. For this application, it is highly desirable to have the proteinaceous material be an antibody or a biologically active fragment therefrom.

Proteinaceous Materials of Interest

Proteinaceous material can be derived from synthetic as well as natural sources such as mammals, amphibians, reptiles, birds, insects and plants, as well as recombinant or transgenic sources. Examples include such materials as a peptides, polypeptides, proteins, antigens, glycoproteins, lipoproteins, or the like (e.g., hormones, lymphokines, growth factors, albumins, cytokines, enzymes, immune modulators, receptor proteins, antibodies including monoclonal antibodies, and antibody fragments or fractions thereof with at least one molecule having at least one ligand site for binding to a metal ion).

Antibody fragments may be advantageous for tissue imaging systems because these antibody fragments permeate target sites at an increased rate. Fab' fragments of IgG immunoglobulins are obtained by cleaving the antibody molecule with pepsin (resulting in a bivalent fragment, (Fab')$_2$ or with papain (resulting in 2 univalent fragments, 2 Fab) (see: Parham, 1983, *J. Immunol.* 131: 2895–2902; Lamoyi and Nisonoff, 1983, *J. Immunol. Meth.* 56: 235–243.) The bivalent (Fab')$_2$ fragment can be split by mild reduction of one or a few disulfide bonds to yield univalent Fab' fragments. The Fab and (Fab')$_2$ fragments are smaller than a whole antibody molecule and, therefore, permeate the target site or tissue more easily. This may offer an advantage for in vivo imaging, since conjugates more readily penetrate in vivo sites (e.g., tumor masses, infection sites, etc.). An additional advantage is obtained when using conjugates formed with antibody fragments because these fragments do not cross a placental barrier. As a result, using this embodiment of the invention, an in vivo site (such as a tumor) may be imaged in a pregnant female without exposing the fetus to the imaging compound.

In one embodiment the protein is preferably one that can cause an immunogenic response in an animal. Examples of such proteins are: bovine serum albumin (BSA), keyhole limpet hemocyanin (KLH), thyroglobulin, immunoglobulin (IgG), etc.

Targeting proteins are known which preferentially bind marker substances that are produced by or associated with lesions. For example, antibodies can be used against cancer-associated substances, as well as against any pathological lesion that shows an increased or unique antigenic marker, such as against substances associated with cardiovascular lesions, (e.g. vascular clots including thrombi and emboli, myocardial infarctions and other organ infarcts, atherosclerotic plaques; inflammatory lesions; and infectious and parasitic agents).

The cancer states include carcinomas, melanomas, sarcomas, neuroblastomas, leukemias, lymphomas, gliomas, and myelomas.

The infectious diseases include those caused by invading microbes or parasites. As used herein, "microbe" denotes virus, bacteria, rickettsia, mycoplasma, protozoa, fungi and like microorganisms, "parasite" denotes infectious, generally microscopic or very small multicellular invertebrates, or ova or juvenile forms thereof, which are susceptible to antibody-induced clearance or lytic or phagocytic destruction (e.g., malarial parasites, spirochetes and the like, including helminths), while "infectious agent" or "pathogen" denotes both microbes and parasites.

Preparation of Binary Conjugate Complexes

The covalent binding of the ligand-containing compound to the proteinaceous material can be achieved by direct reaction of the two materials through reactive sites on both materials. In the case of the proteinaceous material, potentially reactive pendant sulfydryl, hydroxy, phenolic, amino, and carboxy groups can be used as a binding site. When proteins have carbohydrate moieties, oxidizing agents can be used for generating aldehydic sites for subsequent covalent binding with amine derivatives such as primary amines, hydrazine derivatives, hydroxylamine derivatives, phenyl hydrazine, semicarbazide, and thiosemicarbazide groups coordinately bound to a metal ion, thereby providing a water-soluble antibody-metal ion complex.

Binary conjugate complexes are prepared by reacting a proteinaceous material such as a polypeptide, protein, antigen, lipoprotein, an antibody including monoclonal antibody, enzyme, hormone, or fractions thereof with at least one molecule having at least one ligand site. In a preferred embodiment, the proteinaceous material may have multiple sites available for attachment of a plurality of ligand-containing molecules. For in vivo therapeutic and diagnostic studies, monoclonal antibodies produced by a hybridoma technique provide distinct advantages as carriers for imaging systems employing metal chelated binary and ternary conjugate complexes. First, monoclonal antibodies bind only to one molecular site (i.e., an epitope) with specific binding constants. Second, such antibodies are homogeneous and thus are purified with relative ease. Third, monoclonal antibodies can be made in large quantities, and relatively inexpensively, by particular hybridoma lines.

Other, more complex conjugates can be used as exogenous chelators. In these cases, the conjugate must have one site for coordinate complexation with the metal ion and a second, reactive site must be present for attachment to the proteinaceous material. Typically, similar reactive functionalities can be utilized as discussed for the proteinaceous material, but in this case other functionalities that are even more reactive, such as epoxides, azides, or activated acid functionalities, such as esters or acid halides, may also be employed. Preferred in the present invention is the use of ancillary activating reagents, such as carbodiimides, which assist in condensation reactions. The carbodiimide dehydration reaction is further facilitated by the use of an ester forming compound such as N-hydroxy succinamide.

In one preferred embodiment of the invention the conjugated proteinaceous material, also known as a "capture chelator", is immobilized on a substrate that has an affinity for proteinaceous materials. Such substrates or solid phases, (e.g., cellulose or Sepharose), can be composed of materials that are hydrophilic such as polysaccharides, cellulosics; or hydrophobics such as polystyrene; or in the case of antibody proteinaceous materials, antigen-fixed compositions. The substrates can also optionally have reactive sites similar in nature to the reactive sites of the ligand containing compositions discussed supra. In this manner the proteinaceous material is covalently bound to the substrate.

Subsequent to immobilization, an effluent containing the target metal ion is placed in contact with the immobilized proteinaceous conjugate and the metal ion is coordinately bound to the conjugate. In this manner, quantification of the metal ion concentration can be determined.

A preferred conjugated proteinaceous material of the present invention comprises pyridylazoresorcinol (PAR) derivatives of antibody proteins, proteins such as ovalbumin, bovine serum albumin, or enzymes such as alkaline phosphatase. Specifically, when enzymes are utilized in the proteinaceous conjugate, rather than acting as a "capture chelator", the enzyme conjugate is utilized as a "detector chelator" due to the ability of the enzyme to catalyze a variety of reactions that can be readily monitored and thereby quantified. The preferred capture or detection conjugate metal ion complex comprises gallium(III) ions.

In an alternative embodiment to the immediately preceding one, an uncomplexed antibody is immobilized on a solid substrate. Subsequently, a known quantity of serum containing a target antigen species is applied to the immobilized antibody on the substrate causing the antigen to be adhered to the substrate. A second solution containing a complexed antibody as described herein is then administered on the substrate and allowed to associate with the antigen. Any unassociated complexed antibody is extracted, and the remaining complexed antibody is detected and quantified.

In another embodiment, the use of the capture conjugate is useful as an antidote for removal of toxic levels of gallium from animal subjects by in vivo complexation or filtration of the subject's blood through a filtering device comprising immobilized capture conjugate.

In another embodiment of the present invention, the proteinaceous conjugate can be used in an aqueous solution to determine the concentration of metals such as gallium (III), iron(III), and zinc(II). In the latter case, Zn(II) complexes with PAR conjugates are fluorescent, allowing for an assay method that is facile, sensitive, and requires no additional reagents.

In another embodiment of the present invention, a metal ion complexed antibody conjugate is used for diagnostic or therapeutic analysis in vivo in mammalian subjects by administering to the patient an effective dose of the metal ion complexed antibody conjugate via inoculation, oral uptake, or other means. As noted supra, in this case the conjugate should have an affinity for an antigen at the target area. This is typically achieved by having the proteinaceous material comprise an antibody that has specific affinity for an antigen known to be a tumor marker such as carcinoembryonic antigen (CEA), human chorionic gonadotropin or its beta subunit, colon specific antigen-p, tumor specific glycoprotein or the like.

Antibodies in the present invention may be directed against any target (e.g., bacterial, fungal, parasitic, mycoplasmal, histocompatibility, differentiation, and other cell membrane antigens, pathogenic surface antigens, toxins, enzymes, allergens, drugs, and other biologically active molecules). Such metal ion complexed antibody conjugate thereby concentrates locally at the disease site where they can be non-invasively detected by such means as emission tomography, nuclear magnetic resonance imaging, and in vitro spectroscopy. For therapeutic efficacy, the complexed antibody conjugate should contain a radio isotope that emits cytotoxic beta particles or alpha particles.

Ternary Complexes: Protein Conjugate$_1$-Metal-Protein Conjugate$_2$ (PC$_1$-M-PC$_2$)

In another embodiment of the present invention, a ternary complex can be formed by complexing the above mentioned metal complexed binary proteinaceous conjugate (i.e., the capture chelator) with a second protein conjugate, preferably an enzyme conjugate (i.e., the detector chelator) having the same or different ligands from the metal complexed binary proteinaceous conjugate. The enzyme conjugate complexes to the metal ion of the metal complexed binary proteinaceous conjugate to form a "sandwich" or ternary complex.

In one embodiment, the ligand functionality on the detector chelator is the same as on the metal complexed capture chelator. However, most preferred sandwich complexes of the present invention employ two different proteinaceous conjugates. A most preferred ligand is the tridentate pyridylazoresorcinol conjugate, and a most preferred metal ion is gallium(III). A most preferred enzyme is alkaline phosphatase. Other examples include horse-radish peroxidase, β-D-galactodisase, urease, glucose oxidase, and ribonuclease. As with the binary complexes disclosed supra, the ternary complex can be used for detection or therapy.

In a preferred in vitro detection process, the detection chelator is added to the immobilized metal complexed capture chelator and allowed to form a ternary complex. This ternary complex comprises a proteinaceous conjugate, a metal ion and an enzyme conjugate. After formation of the ternary complex, an assaying reagent is added to react with the enzyme portion of the ternary complex in order to form a species that is readily detected and quantified.

In a preferred embodiment the assaying reagent is p-nitrophenylphosphate (PNPP). With the addition of PNPP, enzyme activity doubles between 25 and 37 and the hydrolysis of the PNPP assaying reagent occurs. The products of this hydrolysis reaction are colored inorganic phosphates and the corresponding alcohol, p-nitrophenol, which can be detected at very low concentrations by monitoring its absorption at 405 nm. The concentration of the p-nitrophenol can then be determined by use of the Beer-Lambert Law.

Other colored or fluorogenic assaying reagents that are applicable in the present invention include p-nitro-β-D-galactoside, 4-methyl umbelliferyl-β-D-galactosidase (MUG), o-phenylene diamine, 2,2'-azino-di(3-ethylbenzothiazoline sulfonato-6) (ABTS), o-toluidine, 5-aminosalicylic acid, and o-dianisidine. Other promising new assaying reagents are 3-dimethylaminobenzoic acid (DMAB), and 3-methylbenzothiazoline.

A number of other assaying reagents which yield insoluble products are available for use with alkaline phosphatase enzyme. One such assaying reagent is 5-bromo-4-chloro-3-indoyl phosphate.

The enzymes selected for the present invention can be used to facilitate detecting means by allowing reactions such as acid-base neutralization or redox to generate species that can be detected by such techniques as optical absorption, electron spin resonance, fluorescence, NMR relaxation, or if the metal ion is radioactive, radioactive emission. Many of these same techniques can also be used to detect the binary complexes discussed supra. The enzyme conjugate may optionally be tagged with a substance that fluoresces or emits radiation. In this manner an assaying reagent may not be necessary to quantify the metal ion complexed in the ternary complex.

Alternatively, the activity of the enzyme can be monitored electrochemically. This is because the action of the enzyme on the assaying reagent should result in a change in the observed electrochemistry of the system. The potential limits between which these changes must occur are determined by the medium in which the measurements are performed. This limit is between approximately −0.25V and about +0.90V versus SCE (i.e., between the potentials for the reduction of dissolved oxygen and the oxidation of water respectively).

Other possible electrochemically active assaying reagents for alkaline phosphatase are phenyl phosphate, naphthyl phosphate, and p-aminophenylphosphate (see Bard A. J., and Faulkner, L. R. (1980), *Electrochemical Methods-Fundamentals and Applications*, John Wiley, New York; and Heineman, W. R., Halsall H. B., (1985), *Anal. Chem.* 57, 1321A.) Phenyl phosphate has no electrochemistry within the potential window for aqueous solutions, but its hydrolysis product, phenol, can be oxidized at the potentials around +0.8V versus SCE. When p-aminophenyl phosphate is used, in irreversible wave in cyclic voltammetry at around +0.45V versus Ag/AgCl is usually obtained. But its hydrolysis product, p-aminophenol, has reversible electrochemistry with a half-potential wave of −0.065V versus Ag/AgCl.

Assay Principle

Figure 4:
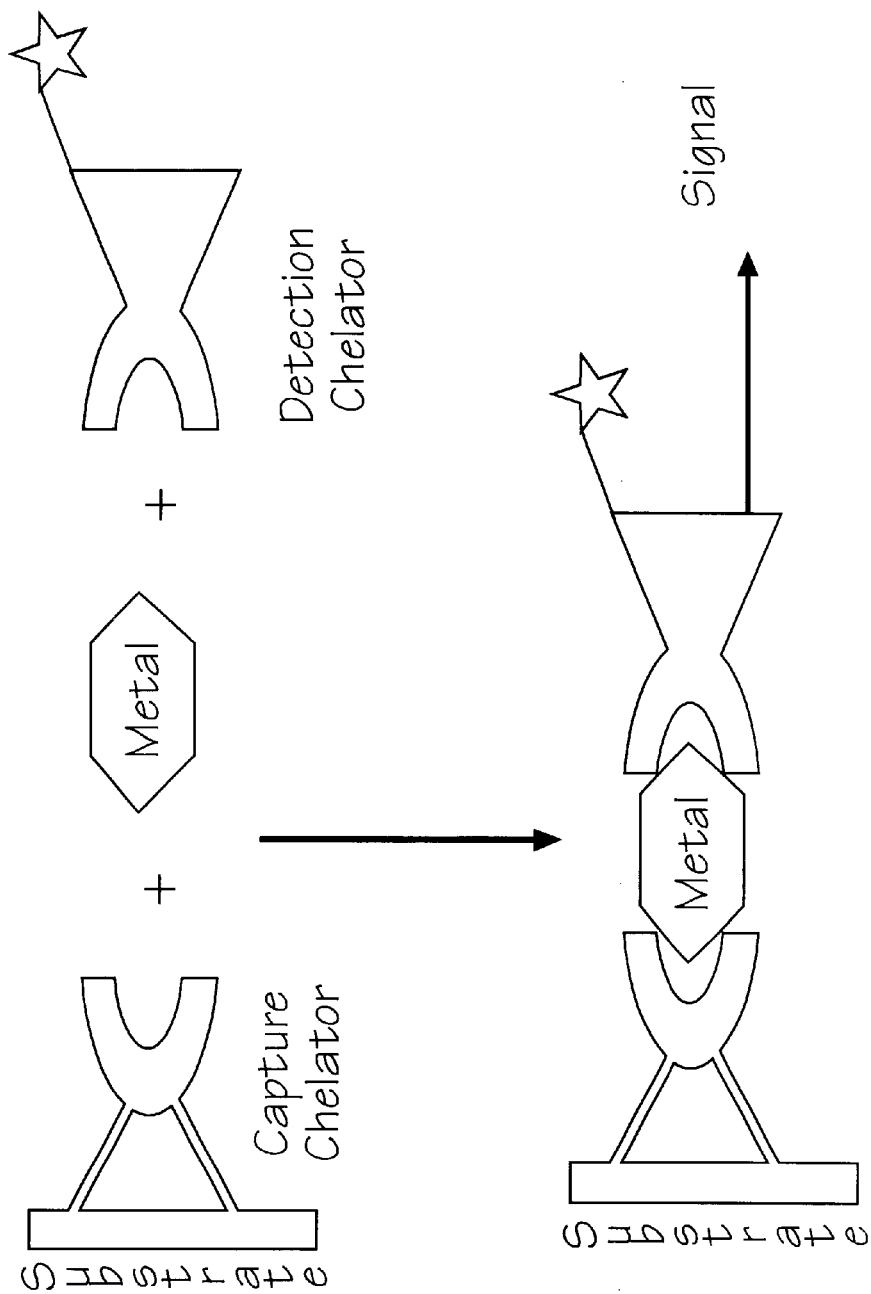
FIG. 4 depicts illustrative examples of ternary, sandwich complexes ($PC_1$-M-$PC_2$)

The detection of Ga(III) using the PAR-conjugate is based on a ternary (sandwich) chelate principle as shown in FIG. 4. In the first step in forming the ternary complex, the metal ion is captured by an immobilized PAR protein conjugate. In the second step, the protein conjugate is detected using an enzyme-labeled PAR-conjugate known as the detection chelator.

The first step of the process for assaying the sandwich is to coat a solid-phase substrate with the protein conjugate, capture chelator (i.e., PAR-ovalbumin (PAR-OVA)), and a metal analyte is incubated with the immobilized according to:

(Equation 1)

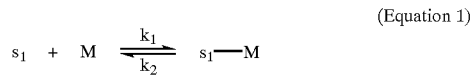

where S1* represents the binding sites of the capture chelator while k1 and k2 are the association and dissociation rate constants respectively. All other sample constituents are washed out and the bound metal analyte is quantitated during the second step by adding the excess detection chelator__(i.e., PAR-alkaline phosphatase (PAR-AP)). After incubation, the PAR-AP is bound to a different site on the metal ion capture chelate molecule according to:

(Equation 2)

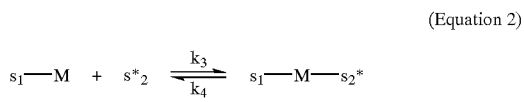

where S2*__represents the binding sites of the labeled conjugate and k3, k4__are the rate constants. Any unbound detection chelator__(PAR-AP) is washed out. The signal is detected by reacting with an assaying reagent which, in one embodiment, produces a measurable absorption enhancement at 405 mn. The signal is directly related to the metal concentration in the sample. Since this assay involves 2 chelators, it provides an improved specificity over a competitive assay principle, because the cross-reactivity substances that nominally interfere with competitive assay produce no signal in the sandwich assay format.

Experimental Details

Reagents

Analytical reagent (AR) grade chemicals were used throughout unless otherwise stated. All solutions were made from Nanopure water having resistivity of 18 MW/cm or higher. The following chemicals were purchased from sources as indicated: 98% (1-(2-pyridylazo)-2-resorcinol (PAR) and 99.99% (4-(2-pyridylazo-2-naphthol from ACROS (Pittsburgh, Pa.); N-hydroxysuccinamide (NHS), Ovalbumin, OVA, (98%)(Lot 371-17015), bovine serum albumin, BSA (>97%, Lot 102H9308), 1-ethyl-3-(3-dimethylaminopropyl)carbodiimide (EDC), $Ga(NO_3)_3$, sodium dihydrogen phosphate ($NaH_2PO_4$, 99%) from Sigma. Others include alkaline phosphatase (AP), Lot#96120639, p-Nitrophenylphosphate disodium (PNPP, 5 mg/tablet (Lot 96111570) from Pierce (Rockford, Ill.); $CuSO_4.5H_2O$, $Co(NO_3)_3.6H_2O$, $Ni(NO_3)_3$, $KNO_3$, $ScCl_3$, In(metal) all from Fisher. $MgCl_2.6H_2O$ (99%) $La(NO_3)_3.6H_2O$, TlCl(99%), $TlCl_3.4H_2O$(98%), $FeCl_3.6H_2O$ from Aldrich Chemicals; and finally $Pb(NO_3)_2$, $BaCl_2.2H_2O$(99.1%), $NH_2OH.HCl$, $FeSO_4.(NH_4)_2SO_4.6H_2O$ from Baker. To remove all traces of metal ions, all glassware were soaked in 3M $HNO_3$ for three days and in water prior to use for one day.

Instrumentation

The characterizations of all protein conjugates, including the enzyme conjugate, were performed using a Hewlett-Packard diode array (Model 8453) UV/vis spectrophotometer equipped with a 1 cm. path-length cell. Protein concentrations were determined using $E^{1\%}_{280}$ with a molecular weight of 45,000 Da for Ovalbumin and 66,400 Da for BSA. Optical densities were measured using a 100-fold dilution to give absorbance readings of 0.1–0.3. Fourier transform infrared spectra of lyophilized samples in KBr pellets were obtained using Perkin-Elmer spectrophotometer (Model 1600 FTIR). For the mass spectrometry characterization, an API III$^{Plus}$ triple quadrupole mass spectrometer (PE-Sciex, Thornhill, Ontario, Canada) equipped with a pneumatically assisted electrospray interface (also referred to as an "ion spray" interface) was employed. The ternary complex system used for the analysis of Ga consisted of a Maxisorb I-96 well microplate, and microplate reader ELX 800 UV plate reader from Bio-Tek Instruments. The plate reader's "instrument control and data analysis" software was from Biotek KC4 Software. The pipettes used were capable of delivering 1 mL and were adjustable in the range 20–200 mL single channel pipette, 0–25 mL adjustable positive displacement pipette, 8-channel 50–200 mL adjustable pipette, borosilicate glass tubes (12×75 mm or 13×100 mm). Labconco, FreeZone 12 Liter, Model 77540 freezer was used for freeze drying.

An analysis to confirm the presence of gallium in biological samples was achieved using an inductively coupled plasma atomic emission spectroscopy (ICPAES) technique. The ICP instrument employed was manufactured by Varian Analytical Instruments purchased from Liberty Spectrometer System (Australia). Gallium detection line of 294.364 nm was employed having lead as the internal standard (line 283.306 nm). The flow rate of argon gas supply was kept at 15 L/min with auxiliary flow rate of 1.5 L/min.

Stock solutions of metals ($1.0 \times 10^{-2}$ M) was prepared by dissolving a calculated amount of the salts (99.99%) in an appropriate amount of 1 M nitric acid. These were diluted to the desired volume and then further diluted to $1 \times 10^{-5}$ M before use. Buffer solution of acetate was used for pH adjustment at 0.1±0.01 M. Stock solution of $Ga(NO_3)_3$ 0.01 M was prepared from 0.2557 g $Ga(NO_3)_3$ plus 2 drops of dilute $HNO_3$ and this was made up to 1 L. The following buffers were used for the preparation of ternary complex standards and enzyme tracer dilution: Carbonate coating buffer having pH 9.6; 0.32 g of $Na_2CO_3$, 0.533 g of $NaHCO_3$, and 0.2 g of $NaN_3$ dissolved and diluted to 1 L; phosphate buffer saline (PBS) pH 7.2, 8.0 g NaCl, 0.123 g $NaH_2PO_4$, and 1.67 g $Na_2HPO_4.7H_2O$; 0.1 M acetate buffer (pH 5.5) 13.6 g of sodium acetate and 1.05 mL of glacial acetic acid diluted to 1 L in a volumetric flask. The substrate solution was made from 9 mL acetate buffer and 1.0 mL diethanolamine, 0.020 g $MgCl.6H_2O$, and 2 PNPP tablets. Sodium acetate (100 mM) buffer pH 5.5 was used both for washing and incubation of standards and samples. The metal solutions used for interference tests were prepared using different amounts of Ga(III) and interference ions.

Preparation of Pyridylazo Methyl Salicylic Acid (PMSA)

Finely powdered 2-aminopyridine (5 g) was dissolved in approximately 5 ml of absolute ethanol and about 6 g of isopentyl nitrite. Sodium (1.2 g) was dissolved in 18.5 ml absolute ethanol. The two solutions were refluxed together for about 2 to 2.5 hours. Unstable diazotate precipitated as a brown solid but was not separated. In addition, about 9 g of methyl salicylic acid was dissolved in a minimum amount of absolute ethanol, while ice-cold ethanol/2-pyridyl diazotate mixtures obtained earlier was added. The crude pyridylazo methyl salicylic acid (as the sodium salt) was separated by filtration and thoroughly washed with ether and dried in vacuum. This product was purified by recrystallization from 1:1 ethanol-water.

Preparation of PAR-Protein Conjugates

PAR-protein conjugates were prepared using a modified procedure previously described by Tijssen and Szurdozi F., Kido H., Hammock B. D., BIOCONJUGATE CHEMISTRY, 1995, G,145–149. This procedure was carried out in two steps. Pyridylazoresorcinol (PAR) was purchased from ACROS and used in the following procedure. In step 1, N-hydroxy succinimide (NHS) derivative of hydroxyl-containing PAR was generated. This was either used directly or stored until needed. In step 2, the reaction of activated PAR with protein was achieved. Briefly, the procedure employed is as follows: in step 1, 0.0235 g (108.5 mmol) PAR was reacted with NHS containing 0.020 g, 173 mmol and also with 0.0249 g (130 mmol) EDC. The mixture was added to 7 ml dry DMF at room temperature with constant stirring for 6 hours. NHS activated-PAR was formed as the carbodiimide became transformed to N,N'-urea. This was later isolated after dilution with water and extracted with ethylacetate to remove carbodiimide, which could deactivate the protein in the subsequent step. During step 2, the NHS-activated PAR and ovalbumin were mixed together at 0° C. for 1 hour in a 0.1 mmol/liter PBS (pH 7.2). The mixture was allowed to react at 4° C. or ice cooled and left overnight. The mixture was extensively dialyzed against phosphate buffer (pH 7.2) to remove the unreacted PAR before being freeze dried. Standard reaction procedures were used to generate the enzyme-labeled chelator (PAR-AP).

Characterization of PAR Conjugates

The UV/vis, IR, and mass spectra (MS) of the PAR-protein conjugate were measured to determine the qualitative difference before and after the conjugation. MS calibration was performed on both the first quadrupole (Q1) and the third quadrupole (Q3) using a solution of polypropylene glycol (PPG) in 3 mM ammonium acetate. Samples were delivered via a 50 micron i.d. fused-silica capillary to the ion spray tip which was held at a potential of +4.6 kV. A syringe pump (Model 22, Harvard Apparatus, South Natick, Mass.) controlled the delivery of the sample at a rate of 5.0 ml/min. The spray tip was positioned 1.0 cm off-axis and 1.2 cm away from the ion sampling orifice (~65 micron in diameter). Compressed air (with pressure set at 45 psi) was employed to assist liquid nebulization. A curtain gas (nitrogen) flow of 1.1 L/min was used in order to prevent moisture from reaching the orifice and the quadrupole guidance lens. The interface (atmosphere-to-vacuum) heater was set at 55° C. Mass spectra were obtained with a dwell time of 2 ms for each step (0.5 Da) in the scan. About 5–10 scans were summed to improve the signal-to-noise ratio. The orifice potential was maintained at 55V in the positive ion detection mode.

Determination of Gallium

The gallium assay described in this work utilized a two-site chelate format as described above. A 100 mL metal-free, PAR-OVA ligand (1:100 dilution) in carbonate buffer pH 9.6 solution was first adsorbed for 12 hours at 4° C. onto a 96-well polystyrene microtiter plate having high protein affinity. The plate was washed with acetate buffer pH 5.5. Solutions of gallium standards were added to each well and the plate was incubated for one hour and then washed in acetate buffer pH 5.5. Several dilutions of PAR-AP were added to each plate and the incubation was repeated for one hour. The plates were washed and an appropriate dilution of enzyme-developer assaying reagent (p-nitrophenylphosphate) was added. The product of enzyme-catalyzed conversion of the reagent was measured spectrophotometrically at 405 nm. In order to optimize the overall assay performance, the effects of pH and the stoichiometry of the PAR chelates were investigated. (See FIG. 5).

Results and Discussion

The assay principle reported here relies on the high affinity chelation of the novel PAR bioconjugate and on a simple immunoassay-based technique to develop a highly sensitive and selective analysis of gallium(III). The use of compounds of 2-pyridylazo and their derivatives are suitable for this purpose because their selectivities can be controlled through an appropriate adjustment of the pH and their strong spectroscopic and luminescence properties. Both PAR and PAN in Scheme I have been widely used as chromogenic agents for determination of metals. In contrast to PAN, PAR and its metal complexes are more water-soluble, thus offering great advantages as chromogenic agents and metal indicators in aqueous media.

Figure 8:
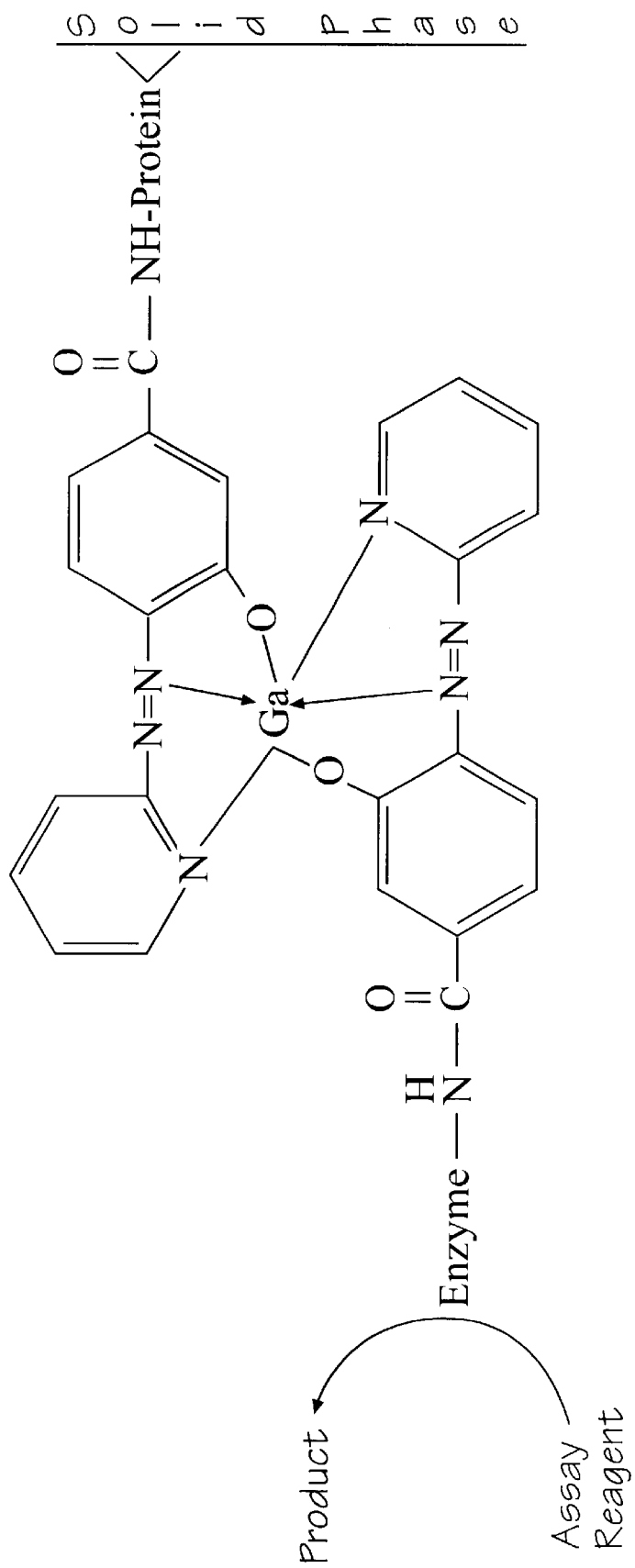
FIG. 8 represents the proposed structure of the gallium-PAR-bioconjugates used in the inventive assay technique, the metal showing a coordination number of six and the binding being through phenolic oxygen, a nitrogen on the pyridine group and a nitrogen on the azo group (tridentate complexation)

Prior to forming protein conjugates, the 2-pyridylazo derivative moiety is not selective, neither as chromogenic agents nor as extractants. However, with appropriate pH adjustment and the use of masking agents, their selectivity can be improved. Masking agents such as hydroxylamine, ascorbic acid, cyanide, fluoride, triethanol amine, and 2,3-mercapto-1-propanol are useful in the present invention. In this case, hydrogen ion competes with the metal ion to combine with the 2-pyridylazo compound. Consequently, the higher the stability of the metal complex, the lower the pH at which it can exist. Also, the lower the pH, the fewer the number of metals that are complexed. The control of pH alone or in combination with masking agents has been used both for selective color formation and extraction. As shown in FIG. 8, PAR forms tridentate 1:1 and 1:2 metal complexes which are coordinated at the pyridine nitrogen, the azo nitrogen farther from the heterocyclic ring and the ortho hydroxyl group. The most stable form of PAR complex is the tridentate 1:2 chelate. As a result of the potential spectrophotometric advantages and chelate formation of 2-pyridylazo and its derivatives, it was decided to investigate its use for conjugation with proteins for specific and selective detection of gallium.

Synthesis and Characterization of Protein Conjugates

Figure 5:
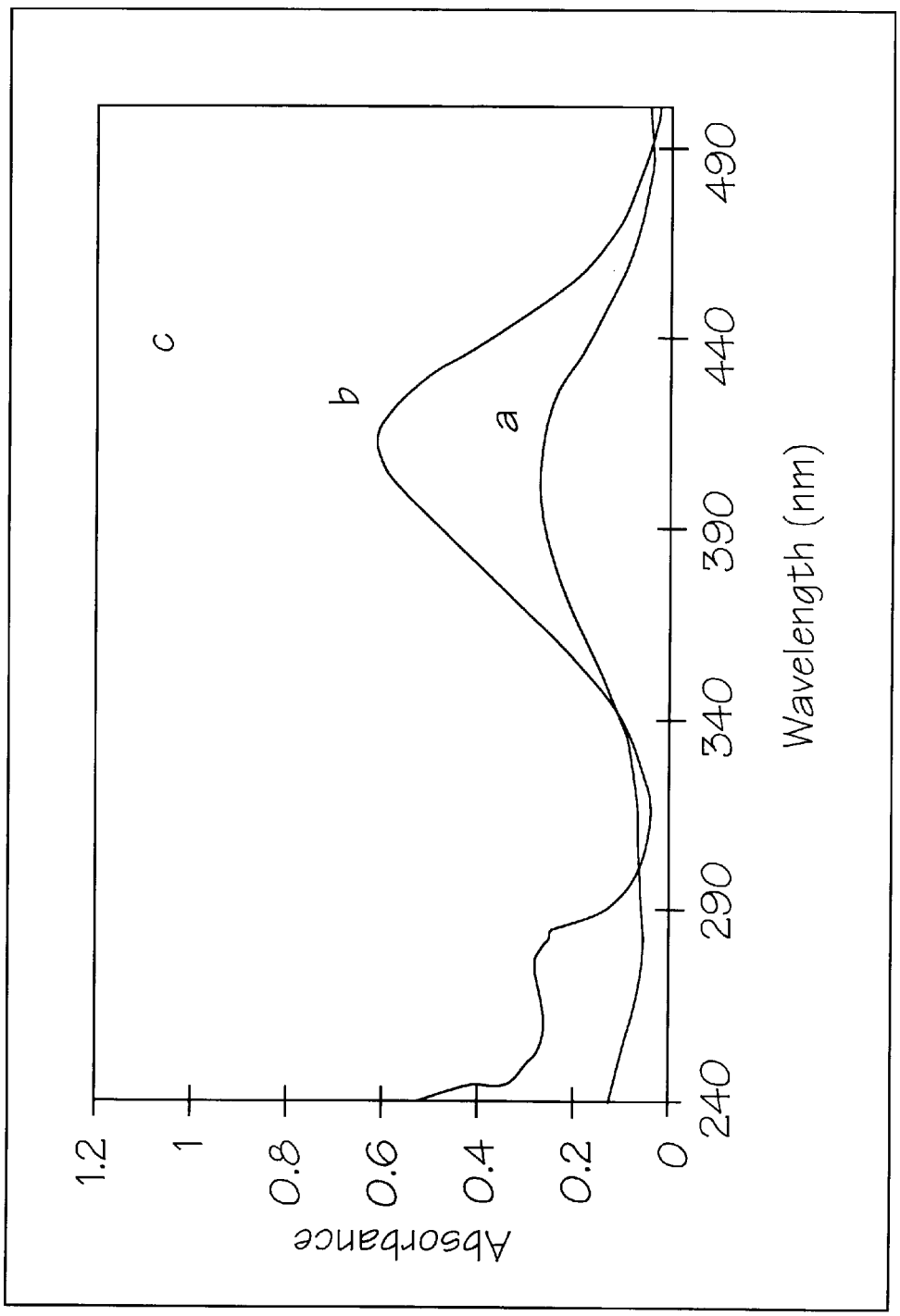
FIG. 5 exhibits UV/visible spectra for PAR and PAR-protein conjugates as described in the Experimental Section; (a) represents $2 \times 10^{-5}$ M PAR, (b) represents PAR conjugated to ovalbumin (PAR-OVA), and (c) represents PAR conjugated to alkaline phosphatase (PAR-AP), phosphate buffer pH 7.2.

Protein conjugates were synthesized as described hereinabove. The UV/vis spectra recorded for PAR-protein conjugates are shown in FIG. 5. Two absorption maxima were obtained at 280 nm for protein and 420 mn for PAR. Results indicated that PAR was successfully conjugated to the proteins. It is expected that PAR should be conjugated to the proteins through its para-hydroxyl group, since it is less hindered. As the para-hydroxyl group is conjugated, the ortho-hydroxyl group is free for complexing with the metal. From the absorbance measurements, the relative ratio of OVA to PAR was estimated to be 3:1 and 1.5:1 BSA to 1 PAR (i.e., mixtures of 1:1 and 1:2 complex) was recorded.

Electrospray ionization mass spectrometer (ESI-MS) was used to determine the molecular weight and fragment ions of the synthetic protein adduct and the accompanying neutral molecules formed during fragmentation. ESI-MS results indicate that PAR was conjugated to the proteins. The ratio of PAR-protein adduct was further confirmed using fast protein liquid chromatography (FPLC) coupled with Fourier transform ion cyclotron resonance (FTICR) mass spectrometry. Results of the FPLC revealed well-defined signals for the protein, which corresponded very well with the molecular weight of the sample. Shortly after the protein eluted, an increase in the conductivity of the solution was observed. This could be attributed to the elution of the salts from the column. The separation of the salts from the protein after solid-phase cleanup helped to improve the quality of the mass spectra, eluting the PAR-Ovalbumin fraction with a corresponding shift in mass corresponding to the PAR-protein adduct. Using a molecular weight of 66,580 Da for BSA, a 1:1 PAR:BSA conjugate was estimated from the ESI-MS measurements. This also corresponded with the degree of conjugation estimated from the UV/V is measurement. The PAR(OVA)$_3$ corresponded to approximately 128, 300 Da, exceeding the detection limit of the instrument.

FTIR experiments were carried out to determine the presence of major amide functional groups in the conjugates. The spectra range was within 4000–200 cm$^{-1}$. Table 1 is a list of the absorption bands obtained. From this table, the most important PAR functional groups are those having absorption bands of stretching vibration frequencies within 1200 and 1230 cm$^{-1}$. These are assigned to the C—OH vibrational modes and N=N— functions (1140–1160 cm$^{-1}$). The presence of both symmetric and asymmetric N-H stretching bands within the range 3550–3450 cm$^{-1}$ and 3450–3350 cm$^{-1}$ were observed for the PAR-OVA, PAR-BSA and PAR-AP conjugates. In addition, Amide II bands with medium intensities arising from deformation modes at 1650–1580 cm$^{-1}$ were also present. The presence of C=O at 1654 and NH at 1530–1539 cm$^{-1}$ showed the characteristic bands of amides derived from the conjugated proteins which were absent from the PAR spectra. The IR spectra of the protein-bonded PAR exhibited a

TABLE 1

Vibrational Frequencies of PAR Ligands and Conjugates (cm$^{-1}$)

| Compound | $v_{C-C}$ $v_{C=C}$ | $v_{C-N}$ | $v_{C=O}$ | $v_{N=N-}$ $v_{N-N}$ | $v_C^{ar}{-OH}$ | $v_C^{ar}{-N}$ | $v_{N-H}$ $v_{O-H}$ | $v_{N-C=O}$ |
|---|---|---|---|---|---|---|---|---|
| PAR ($C_{11}H_9N_3O_2$) | 1472 | 1570 | 1589 | 2304 1150 | 1250 | 760 | — 3444 | — |
| PAR-OVA | 1447 | — | — | 1654 2365 | — | 1447 | 1534 3313 | 1534 |
| PAR-BSA | 1452 | — | — | 1654 2354 | — | 1452 | 1539 3422 | — |
| PAR-AP | — | — | — | 1650 2440 | 1258 | — | 3423 | — | conspicuous feature of a strong, broad band of C—H for protein (3100 cm$^{-1}$), OH (3300 cm$^{-1}$) and C=O (1100 cm$^{-1}$) functional groups which are wider and more intense as a result of the presence of the proteins.

Influence of pH and Evaluation of Formation Constants

Figure 6:
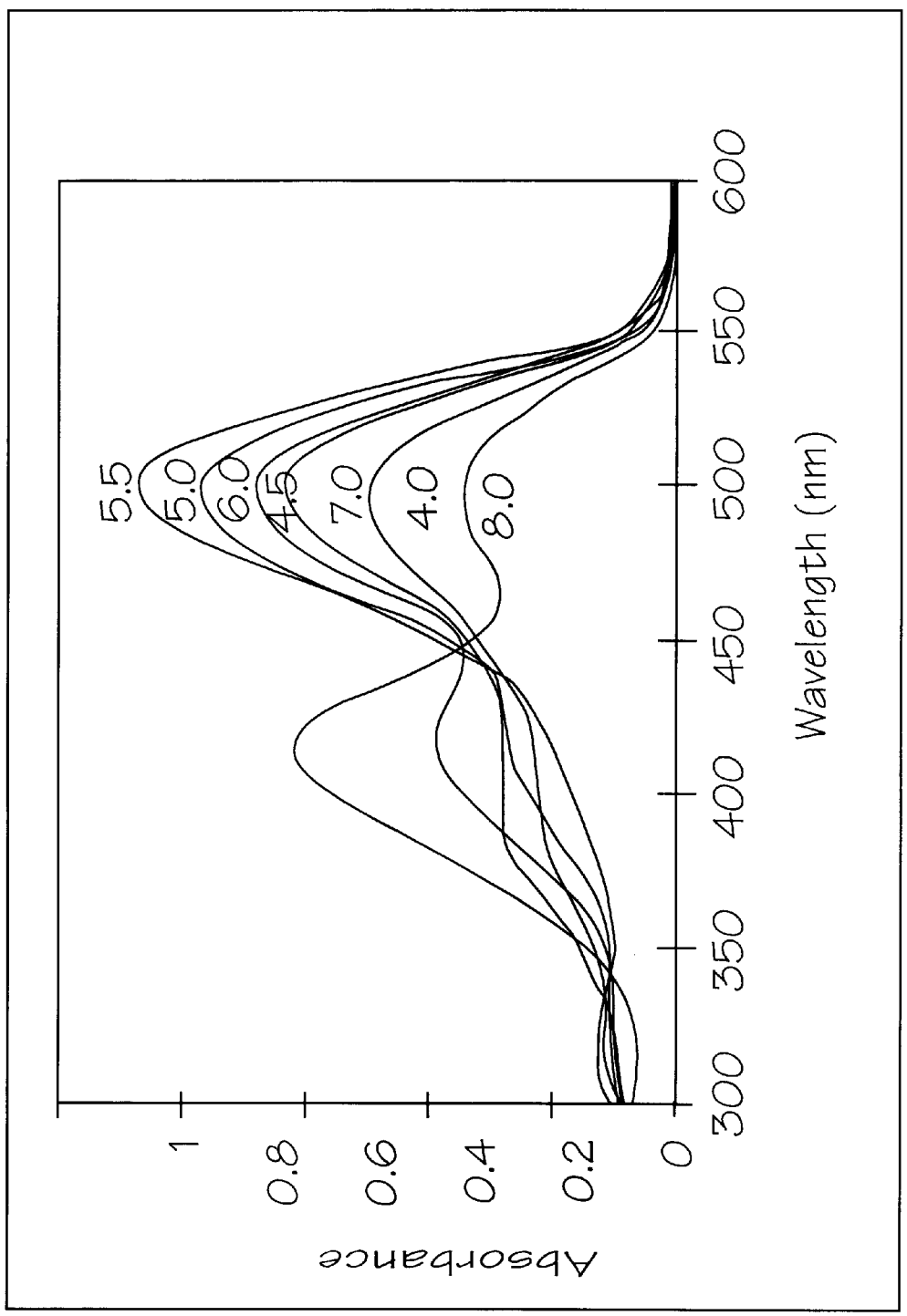
FIG. 6 graphically portrays the influence of pH on the Ga-PAR-protein conjugate absorbance peaks.

The stability of many metal complexes is dependent on pH. The effect of pH on the complexation characteristics of PAR-protein conjugated with Ga was examined using buffered metal solutions in the range 4.5 to 8.0. Evidence of the stability of the conjugates was obtained from the formation constants. At pH 4.0, PAR produced a well-defined complexation effect with Ga as evidenced by the PAR peak at 410 nm, and a wavelength shift at 498 nm (FIG. 6). By changing the pH and subsequent titration with Ga, this peak increased significantly until pH 5.5 and later decreased at above pH 6.0. Similarly, using microplate assay format, the PAR-OVA produced a well-defined complexation with Ga.

Figure 7:
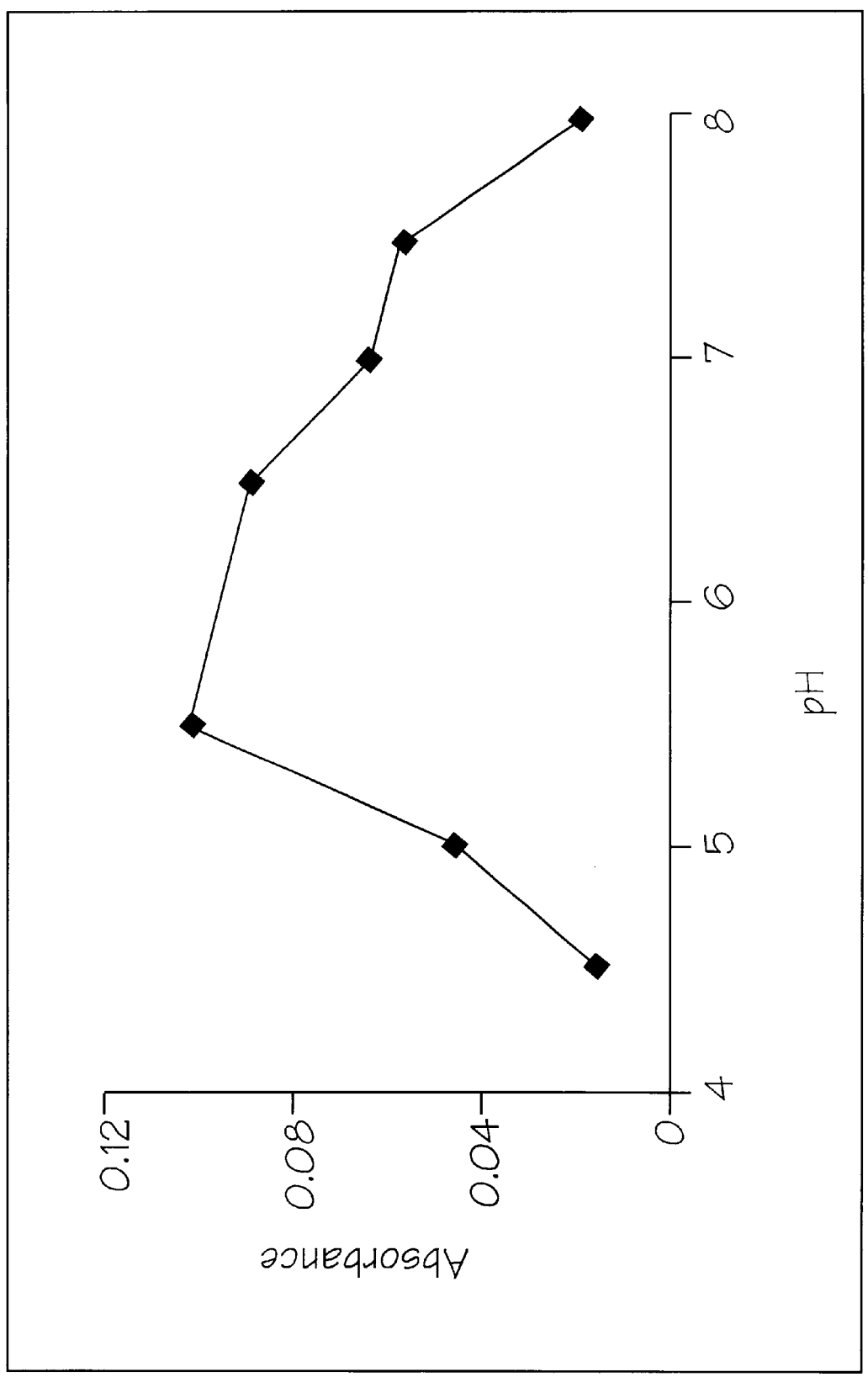
FIG. 7 graphically portrays the quantitative detection of gallium at different pH using the PAR-OVA conjugate.

FIG. 7 shows the results obtained for the quantitative detection of Ga with changes in pH. As the binding slope increased with pH, a peak was formed around pH 5–5.5. At pH>8.0, the quantitative determination of Ga rapidly decreased which could be attributed to a direct consequence of hydrolysis. The optimum pH of 5.5 obtained was then used for further analysis.

The formation constants under the above conditions were calculated from the absorbance data using the method of continuous variation. The color formation was instantaneous and the absorbance values remained constant even up to 72 hours. No significant change occurred when the order of addition of reagent was altered. Using the method of continuous variations, Ga-PAR, Ga-PAR/OVA and Ga-PAR/BSA conjugates were estimated to have the composition 1:2 at pH 5.5 and was confirmed by the mole ratio method. The values of the formation constants of the ligands are summarized in Table 2. The structure of the reagents used in the gallium assay is shown in FIG. 8. Ga forms a strong binding with PAR and the protein conjugates with comparable values to literature data.

Analysis of Gallium using PAR-protein Conjugates

PAR-OVA and PAR-BSA conjugates were used for the analysis of gallium to demonstrate the two-site chelate

TABLE 2

Formation Constants[a] of the Conjugates

| Ligand | pH | Logβ |
|---|---|---|
| Ga-2PAR | 7.2 | 10.3 ± 0.7 |
| Ga-2(PAR-OVA) | 7.2 | 10.2 ± 0.5 |

TABLE 2-continued

Formation Constants[a] of the Conjugates

| Ligand | pH | Logβ |
|---|---|---|
| Ga-2(PAR-BSA) | NA | NA |
| Ga-2(PAR-AP) | 7.2 | 9.9 ± 0.3 |

NA = not available, [a] = temperature 25° C., measurement was conducted in phosphate buffer assay principle described above. The gallium metal was captured by the immobilized PAR-protein conjugate (capture chelator) and this was detected using a second enzyme-labeled PAR-conjugate (detection chelator) at 405 nm.

Figure 9:
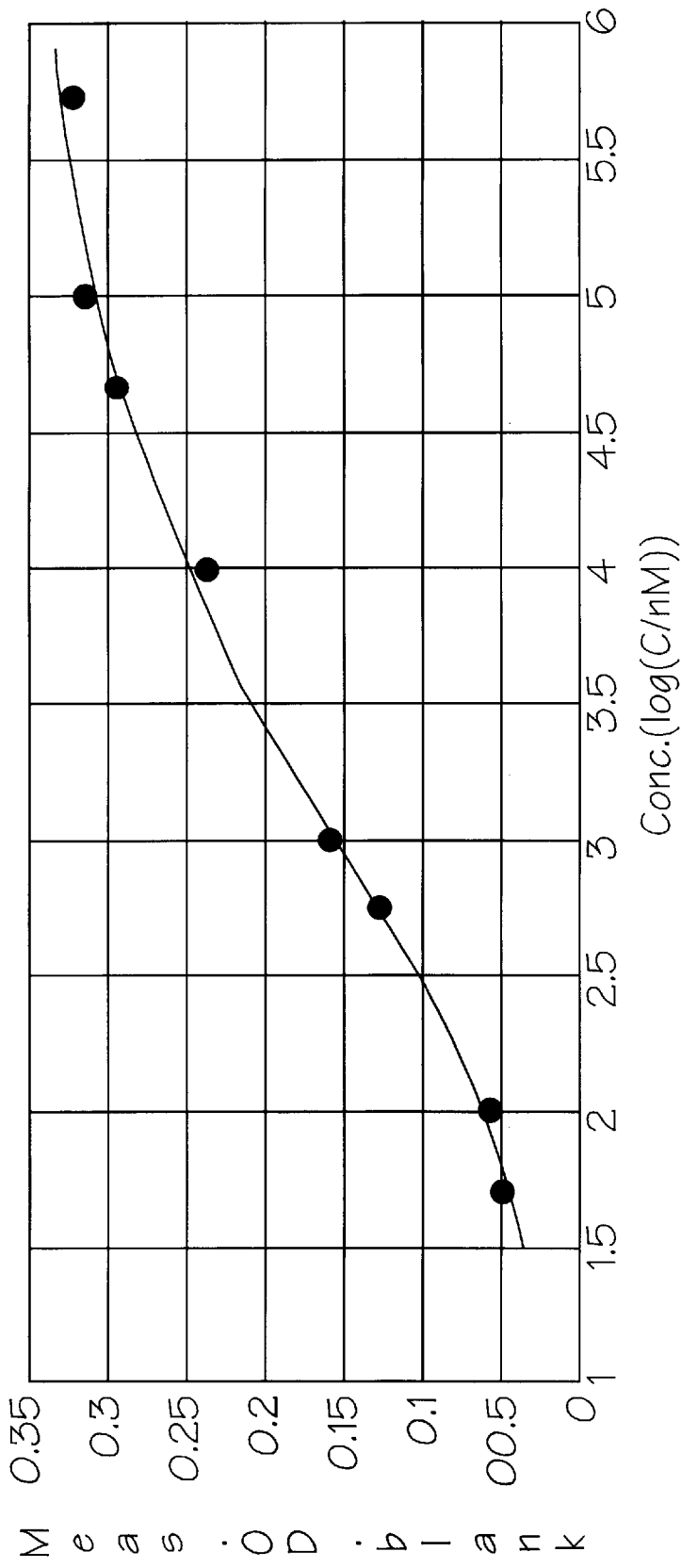
FIG. 9 graphically portrays a 4-parameter fit calibration curve for detecting $Ga^{3+}$ using the PAR-OVA conjugate in acetate buffer pH 5.5.

FIG. 9 represents the standard curve obtained for Ga analyzed using a four-parameter logistic curve fitting. The assay was found to exhibit a characteristic sigmoidal shape and the signal increased with the analyte concentration. At low analyte concentrations, no significant binding occurred and the response was close to that of a zero-gallium concentration. As the concentration was increased, the binding became proportional to the analyte concentration. A plateau was reached when the capture chelator became saturated. Of particular analytical significance was the C value, which represented the value at which the system response was at 50% (or IC50). In immunochemical terms, this is a direct indicator of the general concentration level at which the assay is capable of functioning. This study showed that gallium ions could be conveniently detected with IC50 value of $10^{-6}$M, a linear concentration range of $5\times10^{-7}$ M to $1\times10^{-4}$ M and a correlation coefficient of 0.9980. The assay detection limit which is defined as three standard deviations above the zero standard, was recorded to be $5\times10^{-8}$ M.

Assay Selectivity

Assay sensitivity can be controlled by changing the nature of the immobilized capture chelator. The sensitivities of the quantitative chelate assays for different concentrations were determined using PAR-OVA, PAR-BSA and PAR as the immobilized chelator as shown in FIG. 10. PAR-OVA and PAR-BSA conjugates were found to exhibit significant selectivity for gallium while PAR by itself showed no significant absorbance values beyond that of the blank. The increased sensitivity of PAR-OVA conjugate relative to PAR-BSA could be attributed to the higher ratio of coupling during conjugation. The selectivity of the PAR(OVA)$_3$ conjugates originated from a stronger attachment to the plate, thus decreasing the loss of PAR-protein conjugates during the assay. This attachment stabilized the ligand in the active site and the resulting protein conformational change constitutes the basis for the selectivity observed. In contrast, the relatively weaker attachment of PAR:BSA or PAR(BSA)$_2$ to the plate could result in higher loss of PAR-protein molecules.

The response of the assay to various metals was characterized with respect to gallium. This response is expressed as the concentration of the gallium required to reduce or inhibit the assay response by 50%. This is defined as 50% inhibition $Co^{2+}$ and $Ni^{2+}$ that formed 1:2 ratios with PAR (under optimal pH conditions further from the pH of 5.5 used in the detection scheme) produced no interference. Finally, metals such as $Zn^{2+}$, $Pb^{2+}$, $Tl^+$, $K^+$, and $Na^+$, having ionic radii that are smaller than those of $Ga^{3+}$ and $Fe^{3+}$ produced no signals in the assay.

TABLE 3

Cross-reactivity Data for Ga Determination

| Metal ion | Metal Concentration (nM) | Z | R (pm) | Z/R * 100 | Log K (Metal-PAR Complex) | Stoichiometry (Metal-PAR Complex) | [a]Optimal pH |
|---|---|---|---|---|---|---|---|
| $Ga^{3+}$ | $-1 \times 10^4$ | 3 | 62 | 4.84 | 10.30 | 1:2 | 3.5–8.5 |
| $Al^{3+}$ | $1 \times 10^5$ | 3 | 50 | 6.00 | 11.60 | 1:1 | 5.1–5.5 |
| $In^{3+}$ | $1 \times 10^6$ | 3 | 81 | 3.70 | 9.60 | 1:1 | 6–8 |
| $Zn^{2+}$ | $1 \times 10^7$ | 2 | 74 | 2.70 | 12.60 | 1:1 | 5.2 |
| $Cu^{2+}$ | $1 \times 10^6$ | 2 | 70 | 2.86 | 11.70 | 1:1 | 2.3–5.0 |
| $Pb^{2+}$ | $1 \times 10^7$ | 2 | 120 | 1.67 | 12.90 | 1:1 | 10.0 |
| $Fe^{3+}$ | $<1 \times 10^5$ | 3 | 64 | 4.69 | N/A | 1:2 | 4.0 |
| $Co^{2+}$ | $2 \times 10^6$ | 2 | 74 | 2.70 | 2.90 | 1:2 | 8.25 |
| $Fe^{2+}$ | $2 \times 10^6$ | 2 | 76 | 2.63 | N/A | N/A | N/A |
| $Tl^{3+}$ | $5 \times 10^5$ | 3 | 95 | 3.16 | 9.90 | 1:2 | 4.0 |
| $Tl^+$ | $1 \times 10^6$ | 1 | 140 | 0.71 | N/A | N/A | N/A |
| $Na^+$ | $2 \times 10^7$ | 1 | 95 | 1.05 | N/A | N/A | N/A |
| $K^+$ | $2 \times 10^7$ | 1 | 133 | 0.75 | N/A | N/A | N/A |
| $Mg^{2+}$ | $1 \times 10^7$ | 2 | 65 | 3.08 | N/A | N/A | N/A |
| $La^{3+}$ | $1 \times 10^6$ | 3 | 115 | 2.61 | N/A | N/A | 8.1 |
| $Sc^{3+}$ | $1 \times 10^6$ | 3 | 81 | 3.70 | 12.8 | 1:1 | N/A |
| $Ni^{2+}$ | $2 \times 10^6$ | 2 | 72 | 2.78 | 26.0 | 1:2 | 9.3 |
| $Ba^{2+}$ | $1 \times 10^7$ | 2 | 135 | 1.48 | N/A | N/A | N/A |

N/A not applicable, R values obtained from References 33, 34; K binding constants, Log K, stoichiometry.
[a]optimal pH for the metal-PAR complex obtained from Reference 21.

level or IC50. The result of the cross-reactivity is presented in Table 3 for metals such as $Al^{3+}$, $In^{3+}$, $Zn^{2+}$, $Cu^{2+}$, $C^{2+}$, $Fe^{2+}$, $Tl^{3+}$, $Pb^{2+}$, and $Ni^{2+}$. The data showed that none of the potential cross-reactants exhibited greater that 2500 n cross reactivity relative to gallium (III).

Moreover, the remarkable selectivity exhibited by the bioconjugate may be attributed to the "size-to-charge" (r/z) ratios of the metals. Metals exhibiting comparable r/z ratios to $Ga^{3+}$ should display similar characteristics. The presence of the pyridine nitrogen, the azo nitrogen, and the ortho hydroxyl group enables strong binding with the metal, which is greatly influenced by the charge.

In addition to the size-to-charge ratio, it appears that three other factors may have affected the selectivity for determination of Ga(III). These factors include the binding constant, the pH, and the stoichiometry. Also, the remarkable assay selectivity observed using PAR-protein conjugate is substantiated by actual independent data obtained for the complexation of the different metals tested using the native PAR reagent. These data are shown in Table 3. This also indicates the binding constants (Log K), optimal pH conditions for the formation of metal-PAR complexes as well as the stoichiometry for different metals investigated.

Assuming that the binding between the metal ions and the PAR-protein conjugates is similar to that of the metal ions and the native PAR, then the observed selectivity can be related to those three factors. For example, $Al^{3+}$, $In^{3+}$, $Sc^{3+}$, $Zn^{2+}$, $Cu^{2+}$ and $Pb^{2+}$ ions form 1:1 complexes with PAR and are not expected to produce measurable signals with the PAR protein conjugates. These metals do not interfere with the receptor assay as summarized in Table 3. Only metals that form 1:2 complexes with PAR are expected to give rise to measurable signals in this type of assay scheme. However, Overall, there is a trend between the selectivity recorded in the receptor assay, the binding constants of the native PAR, the size-to-charge ratio, optimal pH, and the stoichiometry. From Table 3, most of the metals did not display signals at least up to 4000 nM that would interfere with the gallium analysis. However, low levels of $Fe^{3+}$ were detected and were removed by reaction with hydroxylamine.

Application

The analytical utility of the PAR-protein conjugates for the analysis of biological samples was tested using spiked reference bovine liver samples.

To 1 g of bovine liver sample, different amounts of Ga(III) solution were added. The mixture was incubated at room temperature for 1 day. The resulting material was digested with 0.5 mL concentrated sulfuric acid and 5 ml, concentrated nitric acid. Hydrogen peroxide, 5 mL (30% v/v) was added in drops during the digestion procedure. The solution was evaporated until all the nitric acid was expelled and dense white fumes of sulfuric acid were observed. The solution was cooled, neutralized by the addition of a 6 M NaOH solution, transferred quantitatively into a 10 mL volumetric flask, and diluted to 10 mL with sodium acetate buffer pH 5.5. Six aliquots of 0.5 mL of this solution were diluted to 2.5 mL each with the sodium acetate buffer, these were used for the 2-site chelate assay as described above.

The analysis to confirm the presence of gallium in the biological samples was achieved using ICPAES. This ICP analysis was conducted using split samples of the digested bovine liver described above except that after digestion, the ICP samples were diluted using Nanopure water in order to minimize interference from sodium ions. Gallium detection line of 294.364 nm was used with lead as the internal standard (Line 283.306 nm).

The results obtained for the recoveries of spiked liver samples using PAR-conjugate chelate assay is summarized in Table 4. A reliable chelate assay was recorded for the determination of Ga(III) in the biological samples. The useful analytical range was in the micromolar concentration at a standard deviation of less than 5% while the percentage recovery was in the range of 97 to 101. From this table, data shown in parenthesis are those obtained in a comparative analysis using ICP technique. Results obtained

TABLE 4

Recoveries of Ga Concentrations from Biological Samples[a]

| Spiked level ($\mu$M) | 1.50(1.95) | 2.29(2.52) | 4.00 | 6.00 |
|---|---|---|---|---|
| Measured level ($\mu$M) | 1.52 (1.95) | 2.27 (2.52) | 4.08 (3.86) | 5.82 (6.36) |
| [b]Recovery (%) | 101 ± 3 (106) | 99 ± 1 (110) | 102 ± 1 (96.5) | 97 ± 1 (106) |
| RSD (%) | 3.10 (NA) | 4.60 (NA) | 4.80 (NA) | 2.40 (NA) |

[a]Measured value for spiked samples was calculated as the sum of the known spike value plus the measured value of the unspiked samples.
[b]Mean ± standard deviation, n = 6. NA = Not available.

from the recoveries of spiked liver samples during ICP experiments were found to be in the range of 96.5 to 110. Higher levels were also obtained for most of the measured concentrations, indicating that these may be subject to matrix interference during the detection of gallium in biological samples. Consequently, these resulted in higher sensitivities for the receptor assay. These results indicate that using these conjugates the 2-site chelate assays may provide a low cost alternative for the characterization of Gallium in liver samples.

Conclusions

In summary, novel protein conjugates have been synthesized. These conjugates were tested for the determination of Ga(III) using sandwich chelate assays format. This method showed very high selectivity for gallium relative to several other metals such as $Al^{3+}$, $In^{3+}$, $Zn^{2+}$, $Cu^{2+}$, $Co^{2+}$, $Fe^{2+}$, $Tl^{3+}$, $Pb^{2+}$, $Ni^{2+}$ and $Tl^+$ ions. Sensitivity in the low parts-per-billion range was recorded with relative standard deviation of less than 5%. The results clearly demonstrate the advantage of using a receptor-based binding assays for very sensitive and selective determination of gallium and the application of this methodology for appropriate determination of gallium in biological matrix.

The successful replacement of an antibody by a protein, which is conjugated to PAR ligand as a recognition molecule, represents a new approach for designing bioassays that will have a wide range of future applications, especially for detecting chemicals that elicit poor immunological response.

Since other modifications and changes varied to fit particular operating requirements and environments will be apparent to those skilled in the art, the invention is not considered limited to the examples chosen for purposes of disclosure, and covers all modifications and changes which do not constitute departures from the true spirit and scope of this invention.

We claim:

1. A protein conjugate gallium (III) complex comprising the reaction product of
   a) a ((heterocyclyl)azo)orthohydroxyarylene derivative comprising a protein binding functionality wherein the azo linking group is attached ortho to the nitrogen atom of the heterocycle and wherein the hydroxy group on the arylene moiety is in a position ortho to the site of attachment of the azo linking group and
   b) a protein
   the conjugate being complexed with gallium (III).

2. The complex of claim 1 wherein the protein binding functionality is selected from the group consisting of hydroxy, amino, sulfhydryl, carboxy, and reactive derivatives thereof.

3. The complex of claim 1 wherein the ((heterocyclyl)azo)orthohydroxyarylene derivative is 4-(2-pyridylazo)resorcinol.

4. The complex of claim 1 wherein the ((heterocyclyl)azo)orthohydroxyarylene derivative is 2-hydroxy-5-methyl-3-(2-pyridylazo)benzoic acid.

5. The complex of claim 1 wherein the protein is selected from the group consisting of antibodies, antibody fragments, ovalbumin, bovine serum albumin, human serum albumin, horseradish peroxidase, and alkaline phosphatase.

6. The complex of claim 1 wherein the complex is immobilized on a substrate.

7. The complex of claim 6 wherein said substrate comprises polysaccharides or cellulosics.

* * * * *